United States Patent [19]
Humphreys-Beher

[11] Patent Number: 5,176,997
[45] Date of Patent: Jan. 5, 1993

[54] DNA PROBE FOR MALE INFERTILITY

[75] Inventor: Michael G. Humphreys-Beher, Gainesville, Fla.

[73] Assignee: University of Florida, Gainesville, Fla.

[21] Appl. No.: 660,465

[22] Filed: Feb. 22, 1991

Related U.S. Application Data

[63] Continuation-in-part of Ser. No. 371,472, Jun. 26, 1989, abandoned.

[51] Int. Cl.⁵ .................... C12Q 1/68; G01N 33/566; C07H 15/12; C12N 9/12

[52] U.S. Cl. ........................ 435/6; 435/975; 435/194; 436/501; 436/94; 536/24.31; 536/23.5; 935/77; 935/78

[58] Field of Search ............ 435/6, 975; 436/501, 436/94; 935/77, 78

Primary Examiner—Margaret Moskowitz
Assistant Examiner—Stephanie W. Zitomer
Attorney, Agent, or Firm—Saliwanchik & Saliwanchik

[57] ABSTRACT

The subject invention pertains to a novel means of identifying male infertility. The novel method involves the identification of a unique restriction enzyme digestion pattern which is highly specific to individuals with male sperm binding infertility.

8 Claims, 1 Drawing Sheet

DNA PROBE FOR MALE INFERTILITY

CROSS-REFERENCE TO A RELATED APPLICATION

This is a continuation-in-part of my co-pending application Ser. No. 07/371,472, filed Jun. 26, 1989, now abandoned.

BACKGROUND OF THE INVENTION

Infertility is a problem that plagues many couples. There are a great number of reasons why difficulty in achieving conception may be encountered, and, because of the complexity of the issues involved, this problem is still very prevalent. In recent years, our knowledge and understanding of the biology and chemistry of fertilization has expanded rapidly. Much of what we know is drawn from in vitro experiments with mouse gametes. It is believed that the strategem described for fertilization of mouse gametes applies to in vivo fertilization of most mammals, including humans.

It is well established that one of the major factors in reproductive failure can be the inability of the sperm to properly associate with, and penetrate, the egg. This type of infertility can be identified by the in vitro sperm binding/penetration assay utilizing the zona pellucida-free hamster egg. While the sperm of some individuals demonstrates a complete inability to penetrate the hamster egg, often there is also an accompanying significant reduction in sperm binding capacity (Kretzer, P., E. Pope, J. B. Younger, R. E. Blackwell [1987] "Long term follow-up of patients with zero hamster tests," The American Fertility Society [Abstract]).

The path leading to fertilization consists of several steps that occur in a precise order. Fertilization begins when sperm associates with ovulated eggs at the cell surfaces. The egg is surrounded by a thick extracellular matrix known as the zona pellucida. Attachment of sperm to the egg appears to be mediated in part by a specific zona pellucida glycoprotein ZP3 (Bleil, J. D., and P. M. Wasserman [1984] Dev. Biol. 104:243-347). The functional group of the glycoprotein is the oligosaccharide moiety of the molecule (Florman, H. M., K. B. Bechtl, and P. M. Wasserman [1984] Dev. Biol. 104:243-247; Shur, B. D. and G. Hall [1982] J. Cell Biol. 95:574). Both sperm adhesion and penetration following attachment are mediated by sperm associated proteins.

Several different sperm proteins are presently under investigation as candidates for the role of mediating egg oligosaccharide binding. All of these proteins are associated with the plasma membrane surrounding the sperm head. Evidence put forward by Shur and coworkers (Shur, B. D., and G. Hall [1982] Cell Biol. 102:1363-1372; Lopez, L. C., E. M. Bayna, D. Zitioff, N. L. Shaper, J. H. Shaper, and B. D. Shur [1985] J. Cell Biol. 101:1501-1510; Shur, B. D., and D. Bennett [1975] Develop. Biol. 21:243-259) suggests that the glycosyltransferase, $\beta$1-4 galactosyltransferase, may in part be responsible for mediating fertilization of the egg by binding N-acetylglucosamine residues in the zona pellucida. Furthermore, sperm capacitation is associated with the release of specific sperm bound galactosyltransferase (GalTase) substrate. The surface transferase is thus exposed for interaction with egg cell-surface glycoproteins during fertilization. In addition, prior galactosylation of the zona pellucida glycoproteins by exogenous galactosyltransferase and UDP-galactose destroys sperm ability to bind to egg (Bayna, E. M., R. B. Runyan, N. F. Scully, J. Reichner, L. E. Lopez, and B. D. Shur [1986] Molec. Cellul. Biochem. 72:141-151).

$\beta$1-4 galactosyltransferase is the most extensively studied of the galactosyltransferases involved in glycoprotein biosynthesis. This enzyme is involved in the addition of O- and N-linked glycoprotein oligosaccharides. Membrane associated galactosyltransferase has classically been localized to the Golgi-apparatus, but a portion of the cellular activity has been found at the cell surface. Numerous reports have suggested that cell-surface galactosyltransferase might be involved in many cellular functions including: cell adhesion (Roth, S., D. J. McGuire, and S. Roseman [1971] J. Cell. Biol. 51:536-547; Pierce, M., E. A. Turley, and S. Roth [1980] In: International Review of Cytology [Bourne, G. H. J. F. Danierl and K. W. Jeon, eds.] pp. 2-44, Academic Press, Orlando, Fla.), recognition (Roseman, S. [1970] Chem. Phys. Lipids 5:270-274), differentiation (Weiser, M. M. [1973] J. Biol. Chem. 248:2536-2549), embryogenesis (Shur, B. D. [1982] In: The Glycoconjugates Vol. 3, pp. 146-185, Academic Press, New York, N.Y.), and fertilization (Shur and Bennett [1975] supra; Bayna et al. [1986] supra).

Although different forms of galactosyltransferase have been characterized according to their localization within the cell, it has not been resolved as to how these different forms are generated. Recent studies suggest that the form of the enzyme may depend on translational differences due to alternate forms of mRNA (Shaper, J. H., G. F. Hollis, and N. L. Shaper [1988] Adv. in Second Messenger and Phosphoproteins Res. 322:39-42) or may depend on the level of phosphorylation of the enzyme (Strous, G. J., P. Van Kerkhof, R. J. Fallon, and A. L. Schwartz [1987] Eur. J. Biochem. 169:301-311.)

Human cDNA which was originally thought to be the clone for the $\beta$1-4 galactosyltransferase gene (Humphreys-Beher, M. G., B. Bunnell, P. van Tiennen, D. L. Ledbetter, and V. J. Kidd [1986] Proc. Natl. Acad. Sci. USA 83:8918-8921) has now been identified as the cDNA of the gene encoding a protein that regulates galactosyltransferase (Bunnell, B. A., D. E. Adams, V. J. Kidd [1990] Biochem. Biophys. Res. Comm 171:196-203; Bunnell, B. A., L. S. Heath, D. E. Adams, J. M. Lahti, V. J. Kidd [1990] Proc. Natl. Acad. Sci. USA 87:7467-7471). This protein has been characterized as a $Ca^{2+}$/calmodulin dependent protein kinase which mediates phosphorylation and influences the activity of surface galactosyltransferase. The protein kinase has been termed galactosyltransferase activator, or GTA.

BRIEF SUMMARY OF THE INVENTION

The subject invention concerns a novel method for identifying male sperm binding infertility. Specifically, this novel method involves the detection of a mutation of the GTA gene. This mutation is responsible for a change in the restriction enzyme digestion pattern associated with the GTA gene. Thus, one aspect of the subject invention involves a simple assay which involves digesting DNA with an endonuclease and, through the use of an appropriate probe, identifying characteristic restriction patterns (RFLPs) associated with male sperm binding infertility.

The identification procedure described here is highly selective in its diagnosis of this type of infertility because the mutation which is detected occurs only rarely in individuals who do not exhibit male sperm binding infertility. These data support the findings of DNA alterations associated with GTA gene expression which may effect sperm function. The methods described here can be used to identify male sperm binding infertility in mammals, including humans.

BRIEF DESCRIPTION OF THE SEQUENCES

Figure 1:
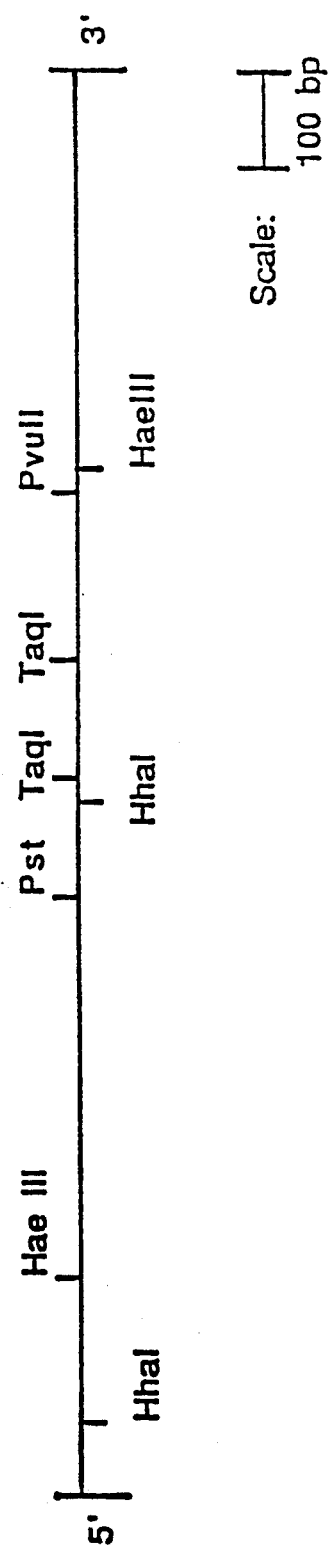
FIG. 1 shows the restriction endonuclease map of human cDNA for GTA. Enzyme restriction sites are indicated along with the 5' 3' orientation of the probe.

SEQ ID NO. 1 shows the DNA sequence and deduced amino acid sequence for GTA.

DETAILED DESCRIPTION OF THE INVENTION

The subject invention relates to a genetic basis for infertility associated with the failure of male sperm to bind and penetrate the egg. Specifically, a DNA allelic variant for galactosyltransferase activator (GTA) expression associated with male sperm binding/penetration infertility has been identified.

A population of human males, whose sperm demonstrated an inability to penetrate ovulated pellucida-free hamster eggs in vitro, were examined for the level of activity of $\beta$1-4 galactosyltransferase. The level of enzyme activity was found to be reduced in human sperm isolated from this group of individuals compared to a known hamster penetration positive group. Analysis of the DNA from these individuals by Southern hybridization with a putative human cDNA clone to $\beta$1-4 galactosyltransferase identified a unique allele lacking 0.8 and 0.4 kb restriction fragments upon digestion with the endonuclease TaqI. Further characterization of the cDNA fragment, including DNA sequencing and amino acid sequencing of the gene product, revealed that the cDNA clone actually hybridized to the gene encoding a protein kinase, galactosyltransferase activator (GTA) (Bunnell & Heath et al., supra), which mediates phosphorylation of, and hence, regulates activity of galactosyltransferase (GalTase). These results represent the first evidence showing that mutations could be associated with the human gene for GTA, a mediator of galactosyltransferase. Despite the finding that the cDNA used in the claimed assay actually codes for GTA, the assay is conducted exactly as originally described, and the results of the assay accurately identify male sperm binding infertility.

One experiment utilized in these studies measures the ability of sperm to penetrate ovulated zona pellucida-free hamster eggs in vitro. Although this hamster egg assay utilizes a zona pellucida-free egg, these eggs contain comparable levels of the saccharide N-acetylglucosamine with the zona pellucida-intact egg, present in cell-surface glycoconjugates. Such levels allow interaction with sperm galactosyltransferase to take place.

The mutation leading to the new allele in association with the gene for GTA appears to lie within the gene itself. The observed correlation of reduced galactosyltransferase enzyme activity in the infertility patients examined could be the result of several different mechanisms acting either directly or indirectly on the enzyme. One possible explanation is that the mutation could be within the structural gene for a protein specifically effecting galactosyltransferase expression and biosynthesis. The correlation of the RFLP and reduced membrane expression in resulting in decreased enzyme activity supports this possible conclusion (see Table 2, infra). Recent studies which show increased GalTase enzyme activity with the expression of GTA, GalTase inhibition in the presence of calcium/calmodulin inhibitors, and amino acid and DNA sequencing data, suggest that our cDNA clone hybridizes to the gene which encodes GTA, a protein which regulates GalTase.

The gene for the GTA cDNA has been mapped to chromosome 4 (Humphreys-Beher et al. [1986] supra). In situ hybridization has placed the gene at p15.2–p15.3. Interestingly, a common fragile site (4p16.1) is in close proximity to this gene which may contribute to an increased mutation rate.

A microorganism, designated hgt2, comprising a cDNA clone for at least a portion of the GTA gene has been deposited with the American Type Culture Collection (ATCC), 12301 Parklawn Drive, Rockville, Md. 20852 USA, on Jun. 5, 1989. The culture was assigned the accession number ATCC 68007 by the repository. The cDNA in this deposited microorganism can be used according to the procedures described herein to practice the subject invention.

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, trhe subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

MATERIALS AND METHODS

Materials. UDP-galactose, bovine galactosyltransferase, ovalbumin, and fetiun were obtained from Sigma Chemical Co.; UDP-[1-$^{14}$C] galactose (specific activity 300 Ci/mmol, [$\alpha$-$^{32}$P] dCTP and [$\alpha$-$^{32}$P] dTTP (3000 Ci/mmol) were purchased from Amersham. Ultrapure agarose and restriction endonuclease enzymes were purchased from BRL. All other reagents were of ultrapure quality and were obtained through commercial sources.

Determination of infertile patient population. Four hundred forty-four couples who had undergone a complete infertility evaluation were found to have no explanation for their inability to conceive. The female partners were found to be ovulatory by biphasic basal body temperature charts, luteal phase serum progesterone evaluations, endometrial biopsies, and mid-cycle sector sonography. They had normal uterine cavities, and were shown to have patent fallopian tubes by salpingraphy. They had no obvious pelvic pathology as evaluated by laparoscopy, and many had undergone simultaneous hysteroscopy. The couples showed normal postcoitus tests, were culture negative for Mycoplasma hemophilus and Ureaplasma urealyticum infections, and negative for immune infertility as determined by a serum IgG test for sperm antibodies. The male partner showed an adequate semen analysis defined as greater than 20 million sperm per milliliter and greater than 40% motility. Finally, spermatozoa from the male partners was tested for its ability to bind to and penetrate the hamster egg cells in vitro (sperm penetration assay, hamster test, humster test). One hundred and forty-one or 32% of the males failed to show penetration of hamster egg cells in vitro. Sperm penetration assays were controlled with multiple known fertile donor sperm, always showing greater than 30% penetration. From this study population, a sample of ten patients and five controls was selected at random for Southern blot analysis of chromosomal DNA.

Galactosyltransferase assay. Sperm-associated galactosyltransferase enzyme activity was assayed as described previously by Humphreys-Beher et al. (Humphreys-Beher, M. G., M. Immel, N. Jentoft, M. Gleason, and D. M. Carlson [1984] J. Biol. Chem. 259:5797-5802; Humphreys-Beher, M. G., C. A. Schneyer, V. J. Kidd, and R. B. Marchase [1987] J. Biol. Chem. 262:11706-11713). In brief, sperm was collected from fresh ejaculate by centrifugation at 500 xg for 10 minutes and capacitated at 37° C. for 24 hours. After collection, the sperm were washed twice with phosphate buffered saline (PBS). The sperm were lysed by sonic disruption and the membrane fraction collected by centrifugation at 100,000 xg for 30 minutes at 4° C. The membrane pellet was resuspended in 10 mM Tris/HCl pH 8.0. A protein assay was performed using a modification of the Lowry protein determination method (Schachterle, G. R., and R. L. Pollick [1973] Anal. Biochem. 51:654-655). The enzyme assay mixture (total volume 50 $\mu$l) contained 0.1M MES (pH 6.3), 25 mM MnCl$_2$, 0.5% TRITON TM X-100, 1 mM UDP-[1-$^{14}$C] galactose (2.0 nCi/mmol), 0.5 mg ovalbumin, and 0-0.5 mg of the membrane preparation. After incubation for one hour at 37° C., the reaction was terminated by the addition of 1 ml ice cold 10% trichloroacetic acid (TCA) and the precipitate recovered on glass fiber filters. Quantitation of incorporated galactose was accomplished by scintillation counting.

Galactosyltransferase labeling of hamster egg membranes. Hamster eggs were collected and used to quantitate the level of galactosyltransferase acceptor carbohydrate moieties on zona pellucida-free and zona pellucida-intact cells. The labeling of intact cells was accomplished by resuspending hamster eggs (50 per reaction) in a total volume of 200 $\mu$l PBS, containing 25 mM MnCl$_2$, 5 $\mu$l of 2 mCi/ml of UDP [1-$^{14}$C] galactose and 5 $\mu$l of autogalactosylated bovine galactosylatrasferase prepared as described by Holt and Hart (Holt, G. D., and G. W. Hart [1986] J. Biol. Chem. 259:8049-8057) and Vittala and Finne (Vittala, J., and J. Finne [1984] Eur. J. Biochem. 138:393-397). The enzyme concentration in the stock solution was 10 units/ml. The mixture was incubated at 37° C. for 30 minutes after which time the amount of labeled protein was determined by lysis of the cells in 1 ml 10% ice cold TCA followed by subsequent collection on glass fiber filters for scintillation counting.

Southern blot analysis of chromosomal DNA. High molecular weight genomic DNA from male infertility patients and fertile male controls was isolated from blood lymphocytes. The lymphocytes were collected from 15 ml heparinized blood by centrifugation at 4500 rpm in a Sorvall (duPont) 3B centrifuge. The cells were incubated in a 5 ml volume of STE (10 mM Tris/HCl pH 8.0, containing 0.1 mM ethylenediaminetetraacetic acid [EDTA] and 150 mM NaCl) buffer containing 0.1% SDS and 10 $\mu$g/ml proteinase K (Sigma Chemical Co.) for 12 hours at 37° C. to lyse the cells as well as degrade protein associated with the DNA. The DNA was recovered by repeated phenol extraction to remove the protein and collected by precipitation with 2.5 volumes of ice cold ethanol. The chromosomal DNA (10 $\mu$g) was digested with the restricted endonuclease TaqI at 65° C. for 24 hours, electrophoresed on a 1% agarose gel and transferred to nitrocellulose by the method of Southern (Southern, E. M. [1975] J. Molec. Biol. 98: 503-515). Hybridization with $^{32}$P labeled nick-translated cDNA probe for galactosyltransferase activator (GTA) clone was performed as described previously at 42° C. (Thomas, P. C. [1980] Proc. Natl. Acad. Sci. USA 77: 5201-5205). The GTA clone employed ($\lambda$-hgt2) comprises a 1.7 kb clone (see FIG. 1 for restriction map). The filter was washed and exposed to X-ray film at −70° C. using intensifying screens for 2-3 days.

cDNA library screening and DNA sequencing. A $\lambda$gt10 cDNA library from rat and mouse testes and liver (Clontech Laboratories, Inc., Palo Alto, Calif.) was screened using a hybridization buffer consisting of 6×SSC (1×SSC=0.015M sodium citrate/0.15M sodium chloride, pH 7.0), 2×Denhardts (1×Denhardts=0.02% Ficoll, 0.02% polyvinylpyrrolidone, 0.02% bovine serum albumin), 0.1% SDS and 0.1 mM EDTA. Hybridizations were carried out at 65° C. using [$^{32}$P]labeled galactosyltransferase activator 1 kb human cDNA fragment (hgt1) as probe (Humphreys-Beher et al., 1986). Filters were then washed in 2×SSC, 0.5% SDS at 65° C. for 2-4 hours and exposed to Kodak X-AR 5 film overnight at −80° C. Positive cDNA isolates were confirmed by Southern blotting of EcoRI digested phage samples and restriction enzyme map comparisons.

DNA sequence analysis was the dideoxy-chain termination method (Sanger et al., 1977) following subcloning into the EcoRI site of M13 mp18 and mp19 (Norrander et al., 1983). Sequencing from template primers in each orientation enabled sequence determination for the entire insert. Sequencing reactions were performed using $^{35}$S-ATP (Amersham) and US Biochemicals Sequenase sequencing kit.

The cDNA coding for GTA can also be obtained by screening human adult and fetal liver (Clontech) $\lambda$gt11 cDNA libraries using methods which are well known to those skilled in the art and which have been described by Bunnell & Heath et al. (supra). The DNA sequence and deduced amino acid sequence for a GTA gene are shown in SEQ ID No. 1.

Following are examples which illustrate procedures, including the best mode, for practicing the invention. These examples should not be construed as limiting. All percentages are by weight and all solvent mixture proportions are by volume unless otherwise noted.

EXAMPLE 1

Phenotypic Identification of Male Infertility that Requires β1-4 Galactosyltransferase As a preliminary step in determining the role of galactosyltransferase in human sperm-binding/penetration assay, a transferase assay was performed using glycoproteins from zona pellucida-free and zona pellucida-intact hamster eggs as galactose acceptor proteins. As shown in Table 1, when exogenous bovine galactosyltransferase was incubated with the zona pellucida-free hamster eggs, the level of $^{14}$C-galactose incorporated in the plasma membrane was approximately 75% of the label incorporated into glycoconjugates of zona pellucida-intact eggs. This observation suggests that the zona pellucida-free hamster egg is an appropriate in vitro model for detecting possible alterations in galactosyltransferase-mediated sperm interactions since the hamster egg retains enzyme substrate saccharides, N-acetylglucosamine.

TABLE 1

Galactosyltransferase substrate activity of zona pellucida-free and intact hamster egg in vitro.

| Substrate[1] | Activity[2,3] |
|---|---|
| Zona-free egg | 977 ± 15 |
| Zona-intact egg | 1397 ± 20 |

[1]Each assay contained 25 hamster ovulated eggs.
[2]Expressed as cpm of $^{14}$C galactose incorporated/hamster egg. Results are based on two experimental determinations perfomred in duplicate. An exogenous source of bovine 4β-galactosyltransferase (Sigma) was used at a concentration of 0.5 enzyme unit/reaction.
[3]Significantly different by T-Test (P = 0.003).

EXAMPLE 2

Identification of a Restriction Fragment Length Polymorphism Associated with the Human β1-4-Galactosyltransferase Activity Following digestion with a restriction endonuclease, DNA isolated from blood lymphocytes can be separated by agarose gel electrophoresis and subsequently probed with a cDNA clone to human GTA. For example, the cDNA clone from hgt2 (ATCC 68007) can be used for this assay. When the restriction endonuclease TaqI is used, two distinct hybridization patterns are observed among the infertile and fertile populations tested. The male population having previously been successful in the hamster egg penetration assay, typically has allele restriction fragment sizes of about 0.8 and about 0.4 kb, along with fragments of about 1.2 and about 2.0 kb. This hybridization pattern is also observed in random samples of DNA isolated from the general population. In contrast, the male infertility patients identified by a failure of sperm to penetrate the hamster egg, have a new allele with restriction fragments of about 2.3 and about 1.2 kb, but lacking the fragments of about 0.8 and about 0.4 kb. The frequency with which this restriction pattern is observed in the general population is less than 5% of the individuals tested.

EXAMPLE 3

Fragments of the GTA Gene

The identification of the unique restriction fragment patterns associated with individuals having sperm binding infertility can be accomplished with probes other than the cDNA clone for GTA described herein and deposited as ATCC 68007. Thus, the procedure described in Example 2 above can be performed using, for example, a fragment of a GTA clone after the test DNA has been digested with TaqI or other appropriate endonuclease. Specifically, it is known that an about 1.0 kb 3' fragment of the GTA clone can be used to detect the restriction fragment pattern after digestion with TaqI. Use of the 1.0 kb fragment isolated by digestion of the cDNA with PstI endonuclease reveals the same hybridization pattern observed when the full length clone is used. Other fragments can also be used so long as these fragments are able to identify a unique restriction fragment pattern resulting from the digestion of a mutated GTA gene with an appropriate endonuclease. For example, fragments of the cDNA sequence of SEQ ID NO. 1 can be used for this purpose. Other endonucleases may also be used so long as a characteristic pattern, which distinguishes the mutant gene from the normal gene, is observed.

Fragments comprising sequences around the TaqI restriction site of the GTA gene can also be used. Polymerase chain reaction methods or other methods of sequence amplification can be utilized in the course of detecting the mutation of interest.

EXAMPLE 4

Sperm Membrane Levels of Galactosyltransferase Enzyme Activity

In order to confirm the link between the observed failure of sperm to penetrate hamster eggs in vitro and the RFLP associated with the GTA gene, we performed an assay for enzyme activity from several individuals of our patient population. As observed in Table 2, the level of galactosyltransferase activity from four individuals demonstrating a failure in the sperm penetration assay also showed a decrease in the specific activity of the enzyme. The level of specific activity in our control population was approximately two-fold higher (Table 2).

TABLE 2

Enzyme activity of sperm-associated galactosyltransferase.

| Sample | Designation | Enzyme Activity 4β-galactosyltransferase[1,2] |
|---|---|---|
| 1 | Normal Hamster Binding | 0.050 ± 0.009 |
| 2 | Normal Hamster Binding | 0.046 ± 0.008 |
| 3 | Normal Hamster Binding | 0.052 ± 0.003 |
| 4 | 0% Hamster Binding | 0.025 ± 0.006 |
| 5 | 0% Hamster Binding | 0.014 ± 0.003 |
| 6 | 0% Hamster Binding | 0.023 ± 0.005 |
| 7 | 0% Hamster Binding | 0.032 ± 0.004 |

[1]Enzyme activity expressed as nmol/min/mg sperm membrane protein. Activity expressed as the result for 3 separate determinations performed in duplicate.
[2]Normal vs. 0%, significantly different by T-Test (P = 0.002).

EXAMPLE 5

Methodologies for Determining Enzyme (GalTase) Activity

Any means by which sperm-associated galactosyltransferase or GTA levels are determined can be used to practice the subject invention. Reduced levels of these enzyme activities indicate the likelihood of sperm binding infertility. Methodologies relying on specific antibodies to galactosyltransferase or GTA can be used to determine the sperm-associated levels of this enzyme. For example, ELISA type tests can be used to make these enzyme determinations. ELISA methodologies are well known in the art. With the knowledge that sperm-associated galactosyltransferase or GTA levels are indicative of male sperm binding infertility, one skilled in the art could formulate and utilize an appropriate ELISA to test for this condition.

EXAMPLE 6
Kits

Kits which could be used for rapid, accurate, and convenient detection of male sperm binding infertility are a further aspect of this invention. These kits could comprise, for example, the DNA probe to be used for the test. Either the full length DNA clone for GTA or a fragment of that full length clone could be included in the kit. The kit could include, for example, a probe to the sequences around the TaqI restriction site of the GTA gene. Polymerase chain reaction methods or other methods of sequence amplification could be utilized in the course of the amplification and detection of the target sequences. The kit could also comprise a supply of endonuclease TaqI to further facilitate the performance of the test.

This type of kit could be of practical use in fertility clinics. The outcome of this test would enable couples and physicians to develop appropriate strategies for in vitro fertilization procedures based on using the husband's sperm as donor. Also, the procedures and kit of the subject invention can be used to screen potential artificial insemination donors in order to separate those who demonstrate this genetic alteration. Thus, a pool with a higher probability of successful fertilization could be created.

EXAMPLE 7
Alternative Applications of the Invention in Other Species

The kit and procedures described here can also be used to detect sperm binding infertility in animals other than humans. Particularly, the procedures could be used for agriculturally important animals which are reproduced using in vitro techniques. Certain other valuable animals might also be likely candidates for these procedures. Thus, the controlled reproduction of cattle and race horses might be enhanced by these procedures.

It should be understood that the examples and embodiments described herein are for illustrative purposes only and that various modifications or changes in light thereof will be suggested to persons skilled in the art and are to be included within the spirit and purview of this application and the scope of the appended claims.

---

( 1 ) GENERAL INFORMATION:

( i i i ) NUMBER OF SEQUENCES: 1

( v i ) CURRENT-APPLICATION DATA:
        ( A ) APPLICATION NUMBER: US 07/660,465
        ( B ) FILING DATE: 22-FEB-1991

( 2 ) INFORMATION FOR SEQ ID NO:1:

( i ) SEQUENCE CHARACTERISTICS:
        ( A ) LENGTH: 3505 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
CGGGTCTGAG  GAGGCATCAG  AGCAGTCCTG  CCCAAGAAGT  AAGTGAGGAA  GAAATGAGTG       60
AAGATGAAGA  ACGAGAAAAT  GAAAACCACC  TCTTGGTTGT  TCCAGAGTCA  CGGTTCGACC      120
GAGATTCCGG  GGAGAGTGAA  GAAGCAGAGG  AAGAAGTGGG  TGAGGGAACG  CCGCAGAGCA      180
GCGCCTGACA  GAGGGCACTA  TGTGCCGACT  CCCCTGCCCT  GTCGCCCATG  GAGCTCAAGC      240
AGGAGCTGCC  CAAGTACCTG  CCGGCCTGCA  GGGTGCCGGA  GCGTCGAGGA  GTTCCAGTGC      300
CTGAACAGGA  TCGAGGAGGG  CACCTATGGA  GTGGTCTACA  GAGCAAAAGA  CAAGAAAACA      360
GATGAAATTG  TGGCTCTAAA  GCGGCTGAAG  ATGGAGAAGG  AGAAGGAGGG  CTTCCCGATC      420
ACGTCGCTGA  GGGAGATCAA  CACCATCCTC  AAGGCCCAGC  ATCCCAACAT  CGTCACCGTT      480
AGAGAGATTG  TGGTGGGCAG  CAACATGGAC  AAGATCTACA  TCGTGATGAA  CTATGTGGAG      540
CACGACCTCA  AGAGCCTGAT  GGAGACCATG  AAACAGCCCT  TCCTGCCAGG  GGAGGTGAAG      600
ACCCTGATGA  TCCAGCTGCT  GCGTGGGGTG  AAACACCTGC  ACGACAACTG  GATCCTGCAC      660
CGTGACCTCA  AGACGTCCAA  CCTGCTGCTG  AGCCACGCGG  GCATCCTGAA  GGTGGGTGAC      720
TTCGGGCTGG  CGCGGGAGTA  CGGATCCCCT  CTGAAGGCCT  ACACCCCGGT  CGTGGTGACC      780
CTGTGGTACC  GCGCCCCAGA  GCTGCTGCTT  GGTGCCAAGG  AATACTCCAC  GGCCGTGGAC      840
```

-continued

```
ATGTGGTCAG TGGGTTGCAT CTTCGGGGAG CTGCTGACTC AGAAGCCTCT GTTCCCCGGG      900
AAGTCAGAAA TCGATCAGAT CAACAAGGTG TTCAAGGATC TGGGGACCCC TAGTGAGAAA      960
ATCTGGCCCG GCTACAGTGA GCTCCCAGCA GTCAAGAAGA TGACCTTCAG CGAGCACCCC     1020
TACAACAACC TCCGCAAGCG CTTCGGGGCT CTGCTCTCAG ACCAGGGCTT CGACCTCATG     1080
AACAAGTTCC TGACCTACTT CCCCGGGAGG AGGCTCAGCG CTCAGGACGG CCTCAAGCAT     1140
GAGTATTTCC GCGAGACCCC CCTCCCATC GACCCCTCCA TGTTCCCCAC GTGGCCCGCC      1200
AAGAGCGAGC AGCAGCGTGT GAAGCGGGGC ACCAGCCCGA GGCCCCTGA GGGAGGCCTG      1260
GGCTACAGGC AGCTGGGTGA CGACGACCTG AAGGAGACGG GCTTCCACCT TACCACCAGG     1320
AACCAGGGGG CCTCTGCCGC GGGCCCCGGC TTCAGCCTCA AGTTCTGAAG GTCAGAGTGG     1380
ACCCCGTCAT GGGGAGAACT CAGCCGGGAC ACAGGCGTGG CTACTGCGG TGGAGCTGCG      1440
ATGAGACTCG GAACTCCTCG TCTTACTTTG TGCTCCATGT TTTGTTTTG TATTTGGTT       1500
TGTAAATTTG TAGAATTAAA TCATTTTCCT TGTAAACCCG AATTCGGGAC CATCACAGTT     1560
TGATTAGCCT CAGCCTCAAG AGCTGGCACA TGCTTGTGAA CTTGTGCTTT CATATTTTCC     1620
TAACCTGTGT GCTCTTTGTG GGAGGAATAA CCCAGACTAG GAATGCCAGC ATCTGCCAAG     1680
CAGTTGGGAT AATTCTTCAC TATTCCACCC TTGCCACAGT ACTATGGGTA GGAGTGACAG     1740
CTCGAAATAT CTACAAACAA GTCACTAAAA AAGCTAAAAG ATGCCAGGAT CCTGATGAAC     1800
CACCACCTCC ACCAAGACCA ATGCTCAGAT TTTACCTGAT TGGTGGTGGT ATCCCCATCA     1860
TTGTTTGCGG CATAACTGCA GGCAGCGAAC ATTAAGAATT ACGGCAGTCG GCCAAACGCA     1920
CCCTATTGCT GGATGGCATG GGAACCCTCC TTGGGAGCCT TCTATGGGCC AGCCAGCTTC     1980
AGCACTTTTG TAAACTGCAT GTACTTTCTG AGCATATTTA TTCAGTTGAA AAGACACCCT     2040
GAGCGCAAAT ATGAGCTTAA GGAGCCCACT GGCCAGCAAC AGAGATTGGC ATGCCAATGA     2100
AAATGGCGAA ATAAATCATC AGGAAATCAT TTCTTTGTCT CTGATTTCTA CATCAGCCTT     2160
GGAAAATGAG CACACTTTTC ATTCTCAGCT CTTGGGGCCA GCCTTACTTT GCTCTTATAT     2220
GTTGCACTGT GGATGTTTGG GGCTTTGGCT GTTTCTTTGT ATTACCCTTT GGACTTGGTT     2280
TTTAGCTTCG TTTTTGGAGC CACAACTTTA AGCTTCAGTG CATTCTTCAT GGTCCACCAT     2340
TGTGTTAATA GGAGGATCT TAGACTTGCG TGGATCATGA CTTGCTGCCC AGGACGGAGC      2400
TCGTATTCAG TGCAAGTCAA CGTCCAGCCC CCAACTCTA ATGGGACGAA TGGAGAGGCA      2460
CCCAAATGCC CCAATAGCAG TGCGGAGTCT TCATGCACAA ACAAAGTGA TTCAACCTTC      2520
AAAATTCCTC CCAGGGCTGC AAATTAACAA ACTTGCAGGC GGCTGCAGCT CAGTGCCATG     2580
CCAATTCTTT ACCTTTGAAC TCCACCCCTC AGCTTGATAA TAGTCTGACA GAACATTCAA     2640
TGGACAATGA TATTAAAATG CACGCTGGCG CCTTTAGAAG TTCAGTTTCG AACAAATGTG     2700
CACTCAAGCC GCCACCATAA AAACAGAAGT AAAGGACACC GGGCAAGCCG ACTCACAGTC     2760
CTGAGAGAAT ATGCCTACGA TGTCCCAACG AGCGTGGAAG GAAGCGTGCA GAACGGCTTA     2820
CCTAAAAGCC GGCTGGGCAA TAACGAAGGA CACTCGAGGA GCCGAAGAGC TTATTTAGCC     2880
TACAGAGAGA GACAGTACAA CCCACCCCAG CAAGACAGCA GCGATGCTTG TAGCACACTT     2940
CCCAAAAGTA GCAGAAATTT TGAAAAGCCA GTTCAACCA CTAGTAAAAA GATGCGTTAA      3000
GGGAAGCCAG CTGTGGTTGA ACTTCAAAAT CAGCAAAAAT CTTATGGCCT CAACTTGGCC     3060
ATTCAGAATG GACCAATTAA AAGCAATGGG CAGGAGGGAC CCTTGCTCGG TACCGATAGC     3120
ACTGGGAATG TTACCACTGG ATTATGGAAA CACGAAACTA CTGTGTAACA TTGCTGGGCT     3180
TCCTAGGCAG AAATTCATAT AAACTGTGAT ACTCACATTC CTTGAAGCTA TGAGCATTTA     3240
AAAACTGTTT ACAGGCACCA TAGGGATTCA AAAGAATTTG GAATAAACTT TGAAGTTTTG     3300
```

```
GATTTTACTT  ATTTTTATCC  CCAAATTGTT  GCTATTTTTT  AGGATCTGAA  ACAAAATCTT      3360

TCTAAAACAT  TGTTTTAGTT  GTCAAAGCAC  CAACAGGACA  TTTTGGGATG  TGAAATGTAA      3420

TTTCTTGGAA  TCTGTAATTT  GTACTTAATA  TTTCAGGCTT  GTATTTAATA  TAATAAATAG      3480

GTGTTTGTTA  AAAAAAAAAA  AAAAA                                               3505
```

We claim:

1. A method for detecting human male fertility or infertility, said method comprising:
   (a) isolating DNA from said human male;
   (b) digesting the isolated DNA with the restriction endonuclease, TaqI;
   (c) electrophoresing the digested DNA on an agarose gel;
   (d) hybridizing the electrophoresed DNA with a probe comprising a cDNA clone having the nucleotide sequence of the full length cDNA insert coding for human galactosyltransferase activator from ATCC 68007; and
   (e) identifying a unique restriction fragment pattern, wherein said fragments are characteristic of said TaqI restriction endonuclease and said pattern is characteristic of either fertility or infertility.

2. The method, according to claim 1, wherein hybridization patterns with restriction fragments of about 2.3 and about 1.2 kb indicate a positive result for male infertility.

3. The method, according to claim 2, wherein said probe comprises cDNA having the nucleotide sequence of an approximately 1.0 kb fragment from the 3' end of the cDNA insert coding galactosyltransferase activator from ATCC 68007.

4. The method, according to claim 3, wherein said probe comprises the cDNA sequence shown in SEQ ID NO. 1 or a 1.0 kilobase 3' fragment of the cDNA sequence shown in SEQ ID NO. 1.

5. A kit for detecting human male infertility comprising cDNA which hybridizes with the gene coding for galactosyltransferase activator wherein said cDNA has the sequence shown in SEQ ID NO. 1 or a 1.0 kilobase 3' fragment of the sequence shown in SEQ ID NO. 1.

6. The kit, according to claim 5, wherein said kit further comprises the endonuclease TaqI, and wherein said DNA and said endonuclease are separately compartmentalized.

7. The kit, according to claim 5, wherein said cDNA comprises the nucleotide sequence of the full length cDNA insert coding for galactosyltransferase activator from ATCC 68007.

8. The kit, according to claim 5, wherein said cDNA comprises an approximately 1.0 kilobase fragment of the nucleotide sequence of the cDNA insert coding for galactosyltransferase activator from ATCC 68007.

* * * * *

UNITED STATES PATENT AND TRADEMARK OFFICE
CERTIFICATE OF CORRECTION

PATENT NO. : 5,176,997
DATED : January 5, 1993
INVENTOR(S) : Michael G. Humphreys-Beher It is certified that error appears in the above-indentified patent and that said Letters Patent is hereby corrected as shown below:

Column 2:   line 58: "resposible" should read --"responsible--.
Column 4:   line 36: "trhe subject" should read --the subject--.
Column 7:   line 29: "perfomred" should read --performed--.
Column 14:  line 12: "claim 3" should read --claim 2--.

Signed and Sealed this

Twenty-sixth Day of October, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,176,997

DATED : January 5, 1993

INVENTOR(S) : Michael G. Humphreys-Beher

It is certified that error appears in the above-identified patent and that said Letters Patent is hereby corrected as shown below:

Column 1, line 3: After the title insert the following:

--The subject invention was made with government support under a research project supported by the National Institute of Health (NIH) Grant No. DE08778. The government has certain rights in this invention.--

Signed and Sealed this

Eleventh Day of January, 1994

Attest:

BRUCE LEHMAN

*Attesting Officer*   *Commissioner of Patents and Trademarks*